(12) United States Patent
Martin et al.

(10) Patent No.: US 9,241,812 B2
(45) Date of Patent: Jan. 26, 2016

(54) CONTROL SYSTEM FOR PROSTHESIS

(76) Inventors: James Jay Martin, Oklahoma City, OK (US); Pravin Chaubey, Edmond, OK (US); David Boone, Seattle, WA (US); Matt Kozlowski, Catonsville, MD (US); Adam Arabian, Silverdale, WA (US)

( * ) Notice: Subject to any disclaimer, the term of this patent is extended or adjusted under 35 U.S.C. 154(b) by 299 days.

(21) Appl. No.: 12/943,733

(22) Filed: Nov. 10, 2010

(65) Prior Publication Data

US 2011/0060421 A1 Mar. 10, 2011

Related U.S. Application Data

(63) Continuation-in-part of application No. 12/776,300, filed on May 7, 2010, now Pat. No. 8,277,515, which is a continuation-in-part of application No. 12/440,581, filed as application No. PCT/US2007/019723 on Sep. 11, 2007, now Pat. No. 8,007,543.

(60) Provisional application No. 60/843,969, filed on Sep. 12, 2006.

(51) Int. Cl.
*A61F 2/80* (2006.01)
*A61F 2/68* (2006.01)
*A61F 2/50* (2006.01)
*A61F 2/70* (2006.01)
(Continued)

(52) U.S. Cl.
CPC ... *A61F 2/68* (2013.01); *A61F 2/80* (2013.01); *A61F 2/50* (2013.01); *A61F 2002/701* (2013.01); *A61F 2002/704* (2013.01); *A61F 2002/705* (2013.01); *A61F 2002/742* (2013.01); *A61F 2002/766* (2013.01); *A61F 2002/769* (2013.01); *A61F 2002/7655* (2013.01); *A61F 2002/7665* (2013.01); *A61F 2002/802* (2013.01)

(58) Field of Classification Search
CPC .............................. A61F 2/80; A61F 2002/802
USPC ............................................................ 623/34
See application file for complete search history.

(56) References Cited

U.S. PATENT DOCUMENTS

| 980,457 A | 3/1911 | Toles |
| 2,696,011 A | 12/1954 | Galdik |
| 2,808,593 A | 10/1957 | Andersen |

(Continued)

FOREIGN PATENT DOCUMENTS

| WO | WO2008011548 | 1/2008 |
| WO | WO2008033337 | 3/2008 |
| WO | WO2008073286 | 6/2008 |

OTHER PUBLICATIONS

First Sensor, Sensor Technics, "Signal conditioning circuitry for the RXU and XSU series sensors", undated.*

(Continued)

*Primary Examiner* — Bruce E Snow
(74) *Attorney, Agent, or Firm* — Lowe Graham Jones PLLC

(57) ABSTRACT

A vacuum pump system for a prosthesis device includes an enhanced suspension mechanism and cooperates with a pressure source, an adaptor assembly, circuitry, and a power source. A virtually air-tight seal between a residual limb and a socket of the prosthesis allows a vacuum fit to be generated by the pump system. The pump system may be controlled with various circuits and processors receiving instructions from a software program. The pump system may be located within a pylon, but yet remain vibrationally and acoustically de-coupled from the pylon.

16 Claims, 14 Drawing Sheets

(51) Int. Cl.
  *A61F 2/74* (2006.01)
  *A61F 2/76* (2006.01)

(56) References Cited

U.S. PATENT DOCUMENTS

| | | |
|---|---|---|
| 5,258,037 A | 11/1993 | Caspers |
| 5,376,131 A | 12/1994 | Lenze et al. |
| 5,549,709 A | 8/1996 | Caspers |
| 5,658,353 A | 8/1997 | Layton |
| 5,702,489 A | 12/1997 | Slemker |
| 5,724,714 A | 3/1998 | Love |
| 5,728,170 A | 3/1998 | Becker et al. |
| 5,735,906 A | 4/1998 | Caspers |
| 5,888,230 A | 3/1999 | Helmy |
| 5,904,722 A | 5/1999 | Caspers |
| 5,980,577 A | 11/1999 | Radis et al. |
| 6,063,125 A | 5/2000 | Arbogast et al. |
| 6,231,616 B1 | 5/2001 | Helmy |
| 6,287,345 B1 | 9/2001 | Slemker et al. |
| 6,508,842 B1 | 1/2003 | Caspers |
| 6,554,868 B1 | 4/2003 | Caspers |
| 6,645,253 B2 | 11/2003 | Caspers |
| 6,726,726 B2 | 4/2004 | Caspers |
| 6,761,742 B2 | 7/2004 | Caspers |
| 6,923,834 B2 | 8/2005 | Karason |
| 6,926,742 B2 | 8/2005 | Caspers et al. |
| 6,974,484 B2 | 12/2005 | Caspers |
| 6,979,355 B1 | 12/2005 | Slemker |
| 7,025,792 B2 | 4/2006 | Collier |
| 7,025,793 B2 | 4/2006 | Eglisson |
| 7,150,762 B2 | 12/2006 | Caspers |
| 7,393,364 B2 | 7/2008 | Martin |
| 2001/0005798 A1 | 6/2001 | Caspers |
| 2002/0087215 A1 | 7/2002 | Caspers |
| 2003/0078674 A1 | 4/2003 | Phillips |
| 2003/0191539 A1 | 10/2003 | Caspers |
| 2004/0167638 A1 | 8/2004 | Caspers |
| 2004/0181290 A1 | 9/2004 | Caspers |
| 2004/0260403 A1 | 12/2004 | Patterson et al. |
| 2005/0131549 A1 | 6/2005 | Caspers |
| 2005/0143838 A1 | 6/2005 | Collier |
| 2005/0197611 A1 | 9/2005 | Taranow |
| 2005/0240282 A1 | 10/2005 | Rush et al. |
| 2006/0212128 A1 | 9/2006 | Nachbar |
| 2006/0212130 A1 | 9/2006 | Collier |
| 2006/0282174 A1 | 12/2006 | Haines |
| 2006/0282175 A1 | 12/2006 | Haines et al. |
| 2007/0055383 A1 | 3/2007 | King |
| 2007/0112439 A1 | 5/2007 | Panucialman |
| 2007/0191965 A1 | 8/2007 | Colvin et al. |
| 2008/0004714 A1 | 1/2008 | Lieberman |
| 2008/0147202 A1 | 6/2008 | Danzig et al. |
| 2008/0221706 A1 | 9/2008 | Scussel et al. |
| 2008/0243266 A1 | 10/2008 | Haynes et al. |
| 2011/0184532 A1* | 7/2011 | Tompkins .................. 623/34 |

OTHER PUBLICATIONS

Limbogic VS Prothetist's Guide; Product Guide; Jun. 12, 2008; PN-2025-H; Ohio Willow Woods, Mt. Sterling, Ohio.

* cited by examiner

CONTROL SYSTEM FOR PROSTHESIS

PRIORITY CLAIM

This application is a continuation-in part of U.S. patent application Ser. No. 12/776,300 filed on May 7, 2010, which is a continuation-in-part of U.S. patent application Ser. No. 12/440,581 filed on Mar. 9, 2009, which claims priority to International Patent Application No. PCT/US07/19723 filed on Sep. 11, 2007, which claims priority to U.S. Provisional Patent Application No. 60/843,969 filed on Sep. 12, 2006, wherein the subject matter of each is incorporated herein by reference in its entirety.

FIELD OF THE INVENTION

The present invention relates to a control system for a prosthetic device, and more specifically to a control system for a prosthetic pump arranged within a pylon coupled to an adaptor.

BACKGROUND

The field of prosthetics, in general, has made great advancements in improving performance on multiple levels for amputees and congenitally deformed individuals. Through these advancements, people across the world are experiencing new aspects of life and reaching new heights of applicability never before thought possible.

Most prosthetic systems, also called prostheses, have a socket that directly interfaces with the prosthesis and a residual limb of the wearer. For purposes of clarity herein, the term "suspension" refers to how the socket and residual limb are coupled to one another. Generally, a firmer suspension increases the effectiveness and efficiency of the interaction of the prosthesis and residual limb. Some common methods of suspension include a suspension sleeve, a locking pin mechanism, a corset, or a suspension belt. However, each of these systems may still have various limitations in versatility and performance.

One relatively successful suspension method incorporates a pump system that utilizes a suspension sleeve to create an air seal between the prosthesis and the residual limb. A small mechanical pump activated during the wearer's normal gait cycle generates a vacuum pressure of up to about fifteen inches of Mercury (50,795 Pascal) on the residual limb. Such a pump system has been found to have superior benefits compared to other, non-vacuum type systems. By way of example, pump systems have been found to promote improved health of the residual limb by increasing circulation.

Further, pump systems may promote a better "fit" of the prosthesis relative to the residual limb. The "fit" of the prosthesis is one of the major issues that must be dealt with whether in the design of the prosthesis, its control logic, its calibration methods, by the interface between the prosthesis and the limb (e.g., liner or gel sock), or any combination thereof. The fit is dependent on volumetric changes of the residual limb, which may be caused by temperature, fluid flow, local stress on portions of the limb, and possibly many other factors. As a result of the residual limb changing in size the prosthesis may slip or undesirably move relative to the limb. Incorporation of a vacuum pump may help reduce or eliminate undesired size changes of the residual limb. Thus, the vacuum pump may allow a better fit of the prosthesis by maintaining an appropriate pressure on the residual limb throughout daily use.

However, pump systems do have some limitations as compared to more conventional, non-vacuum type systems. For example, pump systems may have a less appealing cosmetic or aesthetic appearance, they may be less versatile, they may have a higher mass, and higher audible or inaudible noise levels. In addition, control systems used in conjunction with the pump systems may not adequately replicate or respond to natural human locomotion due to dynamic loading, impact or shock loading, or complex load cycles that may be generated by active individuals.

One conventional prosthesis and method of controlling the prosthesis are described in U.S. Pat. No. 5,724,714. The prosthesis includes an inflatable bladder within the socket. The fit of the prosthesis is controlled by pumping air to or from the bladder in an attempt to improve or maintain a desired fit. While this approach may provide a comfortable fit, it incorporates a dual-socketed system that is spatially bulky and heavy. The inflatable bladder focuses on pre-determined weight-bearing regions of the residual limb, but over time these "pressure points" may lead to residual limb swelling or other undesired changes. Furthermore, this method does not prevent limb volumetric changes, but rather attempts to dynamically react to those changes after they have occurred.

U.S. Pat. Nos. 5,549,709 and 6,231,616 describe pump systems that respectively cooperate with a multi-socketed system. These devices, however, do not incorporate any software control of the pump system and do not have intelligent manipulation of the socket environment. Additionally, they do not incorporate a means of recording environmental changes or use of the prosthesis, amongst others.

U.S. Pat. No. 6,926,742 describes a mechanism for detecting and correcting a drop in pressure in a socket of a prosthesis, but the mechanism may be undesirably noisy when one or more pumps or motors of the prosthesis are turned on.

The eVAC® vacuum type prosthesis, developed by Smith Global, aims to promote a vacuum in the space that is formed between a gel liner and a prosthetic socket by electronic means. The eVAC® prosthesis does not have a mechanism for recording wearer data and does not have intelligent control of the socket environment; instead it is only adjustable with preset settings. Other vacuum type prostheses include the Harmony® VASS™ (Vacuum-Assisted Pump system) developed by TEC Interface Systems and the LimbLogic™ VS remote-controlled vacuum suspension system developed by The Ohio Willow Wood Company.

BRIEF SUMMARY

The present invention relates to a prosthetic pump system or prosthesis that may advantageously provide a better fit and thus increased comfort with respect to a wearer's limb as well as sense and interpret a variety of the wearer's needs. In one embodiment, the prosthesis includes a pump system that evacuates air from spaces, gaps or other interstices present between the residual limb and the prosthesis while increasing a surface contact area between the same, which in turn may minimize undesired size changes of the residual limb. The pump system may be used in either upper or lower amputee prosthetic pump systems. The pump system may achieve an appropriate fit (i.e., desired suspension) through the use of a circuit, pump, embedded software, and power means. The prosthesis may further include sensors, electronics, software or other components that provide the ability to record, monitor, analyze, and maintain a vacuum fit and the parameters, inputs or other variables associated with such data may be monitored, revised, or otherwise manipulated with a graphical wearer interface.

In one aspect of the present invention, a prosthetic device includes a prosthetic socket engageable with an amputated limb; a pump system having a vacuum chamber; a pylon coupled to the prosthetic socket to define a cavity located proximal to the limb, the pylon defining a cavity sized to receive the pump system for the prosthetic device; and an adaptor configured to minimize an overall lengthwise dimension of the prosthetic device and interface with the pylon, the adaptor coupled to at least a portion of the pump system, the adaptor having an interface that permits fluid communication between the socket and the vacuum chamber.

In another aspect of the present invention, a prosthetic device having a socket assembly includes a pylon coupled to the socket assembly, the pylon defining a housing with an internal cavity; a pump system having a vacuum chamber located in proximity to the socket assembly, the pump system positioned within the housing, the vacuum chamber in fluid communication with the socket assembly; and an adaptor clamped around an outer surface of the pump system and also coupled to the pump system, the adaptor configured to structurally support at least a motor for the pump system within the pylon.

In yet another aspect of the present invention, a method of controlling a prosthetic vacuum suspension device includes the steps of (1) sensing a pressure level in a prosthetic socket and controlling the pressure with a pump located within a pylon of the prosthetic device; (2) sensing at least one non-pressure parameter of the prosthetic device; (3) determining a present activity pattern based on the sensed data; (4) selecting a known activity pattern based on the determined present activity pattern; and (5) selectively adjusting pressure limits for the pressure level in the prosthetic socket based on a comparison of the present activity pattern with the known activity pattern.

In still yet another aspect of the present invention, a control system for a prosthetic device includes a pressure sensor arranged to determine a pressure within prosthetic socket of a prosthetic vacuum suspension system; a non-pressure sensor arranged to determine a parameter corresponding to a dynamic response of the prosthetic device; a controller in signal communication with the sensors, the controller configured to analyze signals received from the sensors over a desired period of time, the controller further configured to calibrate the suspension system based on a type of activity presently engaged in by a user, wherein the calibration includes comparing the analyzed signals relative to data from a known activity; and a vacuum pump of the suspension system operable to change the pressure within the prosthetic socket based on instructions from the controller.

In yet another aspect of the present invention, a method of fitting a prosthetic device includes the steps of (1) sensing a pressure level in a prosthetic socket of the prosthetic device; (2) analyzing the pressure level over a period of time to identify any undesired pressure gradients while ambulatory; (3) determining a quality of fit for the prosthetic device based on the analyzed pressure levels; and (4) providing notification of an overall fit characteristic between the limb and the prosthetic device. The method includes providing notification to one of either a patient or a prosthetist of a potential failure mode, and providing at least one of a visual or audible signal to a patient or a prosthetist to indicated the potential failure mode after a triggering event.

BRIEF DESCRIPTION OF THE DRAWINGS

The invention will be better understood and objects other than those set forth above will become apparent when consideration is given to the following detailed description thereof. Such description makes reference to the drawings in wherein.

DETAILED DESCRIPTION OF THE INVENTION

Figure 1:
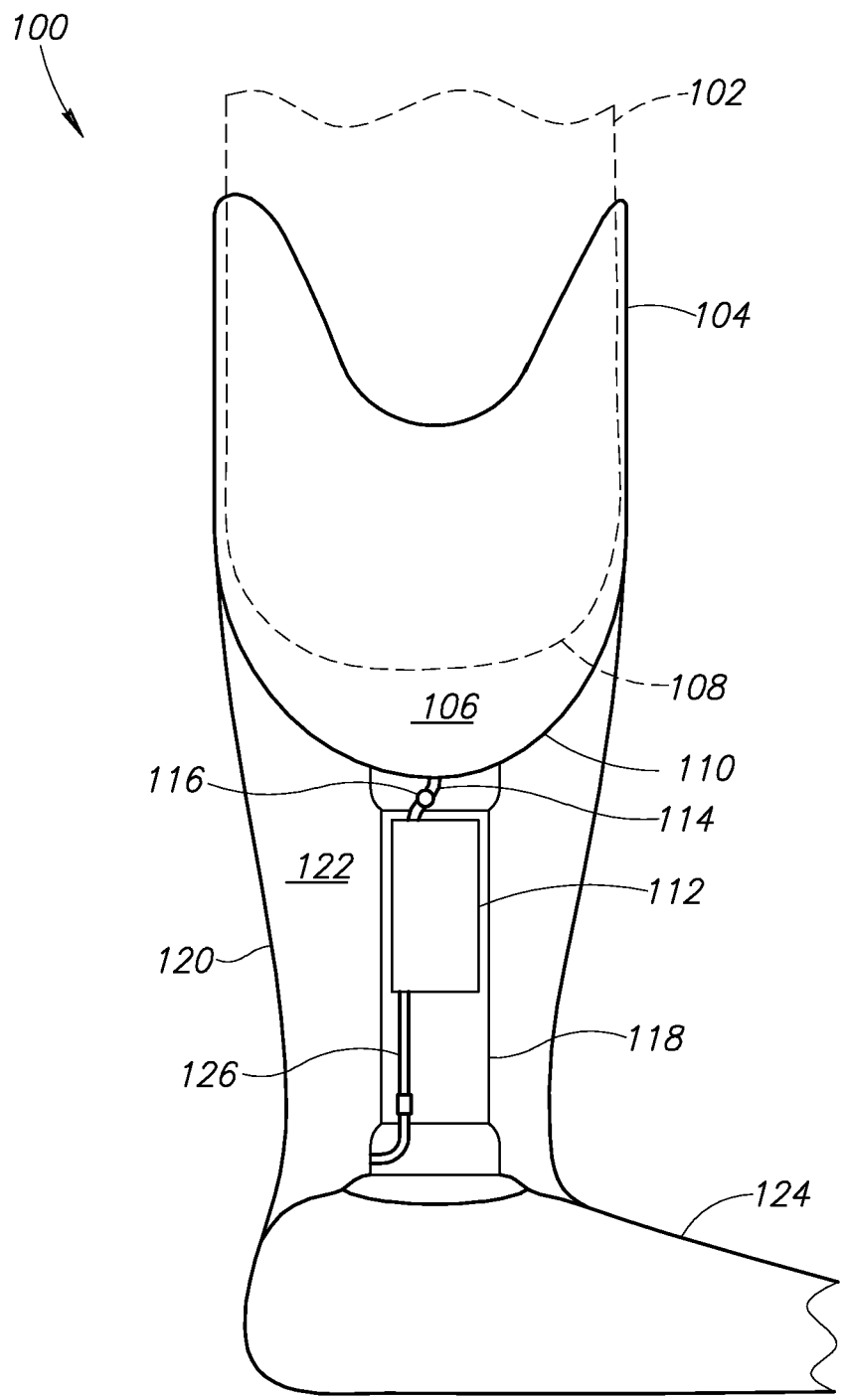
FIG. 1 is a general side view of a preferred embodiment.

This disclosure, in general, describes a new and improved vacuum pump system that provides enhanced suspension and, in turn, a more effective and efficient prosthetic limb application. The pump system may advantageously provide an amputee with a safer and more comfortable fitting prosthesis that may have better proprioceptive control and feel as though the prosthesis is an extension of the wearer's own body.

In one embodiment, a prosthesis integrates a socket, circuit, vacuum pump system, pylon, and power means while incorporating acoustic dampening and data collection capabilities. The processed data may permit a better fit of the prosthesis, for example tailored for each individual wearer. Further, the pump system includes a means for actively altering a vacuum pressure, in which such alterations may be initiated by the wearer, a prosthetist, a control system corresponding to environmental changes, or any combination thereof. Preferably, the pump system is sufficiently small, lightweight, and easily concealed within the prosthesis as to cosmetically integrate therewith. The pump system may further allow for feedback from the wearer.

The pump system may automatically monitor and maintain a desired vacuum pressure between the wearer and prosthesis. Additionally, the pump system may record and analyze data that may be processed to optimize or at least attempt to optimize fit, usability and other functions of the prosthesis for the wearer. By way of example, the "usability" of the prosthesis has been identified as one of the most important characteristics of the prosthesis by amputees, thus the pump system may permit the wearer to circumvent changes that would otherwise be commanded by the control system.

The pump system may be utilized with an upper or lower prosthesis and may have a lower manufacturing cost with regard to conventional pump systems. The lower manufacturing cost may result from material changes, reduced assembly time, and/or other factors. The pump system may also be configurable to require less training time to operate, maintain and adjust while providing consistent performance for and minimal operating noise audible to the wearer.

The prosthesis may generally include a socket in fluid communication with a pump system, a circuit in signal communication with control software, and a power source. In one embodiment, the pump system evacuates air from a space that exists within the socket to provide a secure fit and improved suspension.

One aspect of a comfortable and properly fitting prosthesis is a complete or near complete air tight seal between the prosthesis and the residual limb. In one embodiment, this fit may be achieved with a sealing suspension sleeve, a dual layer liner, or another device that may utilize a self sealing liner, a compression ring, or other form of sealing. For example, around the residual limb there may be a gel liner that is partially covered with a sock, hose, or other porous covering so that the top few inches may be exposed. The porous covering may allow air to wick within the pump system and therefore provide a substantially uniform vacuum. The socket may be configured to fit securely with the liner and porous covering. A nonporous suspension sleeve or similar device may initially hold the socket to the limb to provide sealing with respect to the pump system, the gel liner, and the skin of the residual limb. This may provide a virtually air tight system.

In one embodiment, a vacuum is pulled from the socket through a small hole, channel and/or an air-permeable area protruding from the socket. It is preferable that any air leak be substantially minimized or prevented as between the socket and the pump system. The pump system may include a filter to prevent unwanted or otherwise extraneous particles from entering a vacuum pump of the pump system. In addition, the pump system may include a valve to promote and retain a desired vacuum pressure within the socket. By way of example, the valve may take the form of a one-way valve or check valve that allows air to exit the socket, but not re-enter.

The vacuum pump of the pump system may take the form, but is not limited to, a linear actuator driven pump, an artificial muscle driven pump, an electro-active polymer or other material driven pump, a non-motor driven pump, one or more electric diaphragm pumps that may operate in series, respectively, or some other type of pump capable of obtaining the desired vacuum pressure in the socket and adjusting that pressure to a desired level.

A pylon for housing the pump system may include vibration dampening, acoustic dampening, or both located in proximity to a motor of the pump system. In one embodiment, the pylon includes a variable inner diameter configured to house the pump system.

The acoustic dampening may include, but is not limited to, sound proofing foam or fiber wrapped around the vacuum pump, motor, or both. The foam may be a silicon or similar material capable of absorbing acoustic energy. In another embodiment, the acoustic dampening takes the form of a silencing device fixed to the pump system. Alternatively, acoustic dampening may be achieved by affixing or encompassing a cosmetic covering or casing to the outside of the pump system which may reverberate the noise in directions other than outwards, or simply dampen the sound generated from the pump. Additionally, the use of a mass encasement to encompass the pump may be arranged in preferably an air-tight manner, such that the encasement dampens sound transmissions attempting to travel therethrough. Combinations of the aforementioned may also be used to dampen vibration and/or acoustic transmissions from the pump system. In another embodiment, the encasement may have a vacuum drawn about the pump to prevent sound transmission—since sound cannot be transmitted through a vacuum given that no vibratory effects are the cause of sound transmission. The pumps of the pump system may operate to draw a vacuum in both the socket and the encasement. Yet another method for acoustic and/or vibration dampening may include slowing down the pump actuation or motor to change its acoustic signature transmission.

Additionally, the encasement for the pump system may include other prosthetics components such as a pylon or housings of other prosthetic devices. Typically, the pylon is of a round, hollow nature and aids in the support and strength of the prosthesis structure. The pylon may be configured, by changing its mass or stiffness for example, to provide for additional or alternative sound mitigation and possibly to provide enhanced structural support for the prosthesis. In one embodiment, an inner wall of the pylon may be configured as a cylinder to house a piston of the pump system.

A preferred embodiment may include several possible pressure controlling mechanisms. One such mechanism incorporates a variable vacuum switch with a fixed dead band. By way of example, if the pump system maintains a vacuum pressure of 21 inches of Mercury within a range of ±4 inches of Mercury, the vacuum pressure should be monitored such that it can be controlled to turn ON or OFF at a desired time. By setting a fixed dead band, the vacuum pressure may increase to a level in which the pump system becomes disabled. Thus, as the vacuum pressure slowly diminishes, it will reach a threshold in which the fixed dead band is reached. At that time, a signal transmitted to the pump system reactivates the vacuum pressure to bring it to the same or a different desired level. This control process allows for the vacuum pressure to be operated only under necessary measures to conserve energy and reduce operating noise.

Another pressure controlling mechanism may involve using a pressure sensor incorporated into a microprocessor controlled system that includes a range of pressure limits, which may be selectively set or pre-programmed. By way of another example, when the vacuum pressure is in a set pressure range the pump system deactivates. Upon reaching a predetermined limit or threshold, a pressure sensor detects a shift and relays an analog, or other, signal to the microprocessor, which in turn relays a signal to the pump system to re-activate. The set pressure range may be adjustable depending on a variety of characteristics, demands or other factors of the prosthesis. Additionally, an upper and lower threshold of the pressure range may be independently adjusted through multiple means such as, but not limited to, electronic resources, manual resources, dials, switches, sensors, graphic wearer interface, etc.

Stated otherwise, the thresholds defining the pressure range may be actively adjusted in order to provide a greater suspension to the limb and/or in reaction to forces applied to the prosthesis. This variability in the thresholds may be preset, correspond to algorithms of the control system, or both. For instance, when the wearer of an upper-extremity prosthesis picks up an object having sufficient mass, the pump system reads that a load has been applied and interprets the load as an indication that the prosthesis is tending to be pulled away from the residual limb. In turn, the pump system initiates or turns on the vacuum pressure and/or increases a magnitude of the vacuum pressure to provide a desired amount of suspension.

Furthermore, a means of data recordation may be incorporated within the prosthesis. In one embodiment, a microprocessor or microcontroller having a memory are provided in the prosthesis. The microprocessor receives data from the pressure sensor, processes the data, and records the data in the memory. The recorded data may then be accessed by an external computer or other device which may further process the information. In this manner, prostheses may be tailored to the individual needs of each wearer based on the day-to-day activities of that individual. The external computer could communicate with the pump system by multiple methods including, but not limited, to a USB port, a wireless signal such as Bluetooth, or other means. The wireless signal would allow both the wearer and prosthetic fitter easier access to the data and an interface to adjust or set various parameters related thereto. The wireless method may be activated for a given, or settable, period of time after the computer has been disconnected from a power source, or turned on, or other methods of defining a given usability moment which may initiate the use of the wireless communication system. Additionally, the attachment of the power source may automatically download information from the prosthesis to another storage device or computing system.

A software and Graphical User Interface (GUI) system (hereinafter referred to as a software system and GUI system, respectively) may also be incorporated in the prosthesis. The GUI system may be in direct interaction with a circuit board and microprocessor. The software may be configured to receive the wearer's information, such as, but not limited to, the wearer's name, date and time of last adjustment, date and time of last meeting with the prosthetist, and activity-related data of the wearer. The software may additionally retrieve settings from the circuitry and microprocessor and update with new settings. The GUI system settings may include a setting for changing the minimum vacuum pressure that the prosthesis can be at before the pump system restarts. Furthermore, a maximum vacuum pressure may be set, indicating an upper limit under which the prosthesis can maintain its fit to the residual limb for normal use, and can use alternative thresholds/algorithms for specialty use such as but not limited to greater force being exhibited on the prosthesis as discussed above.

Additionally, a control program may monitor temperature and/or humidity/perspiration within the socket and consequently initiate the pump system based on these or other parameters, which may be individually sensed, detected or measured. Even furthermore, these systems may incorporate a systematic method of variably adjusting the vacuum pressure throughout the day in order to promote adequate circulation in the residual limb. For example, such a method may provide variable vacuum pressures on the limb throughout the day so that the residual limb tissue experiences force changes, which in turn should increase local blood flow.

A setting for a time period of pressure check frequency and a data record frequency may be included to allow the prosthetist to view various graphical representations of the vacuum pressure change over various time limits. Such date may indicate an average period of time under which an acceptable vacuum pressure fit) is maintained and may also indicate whether or not a leak or malfunction in the pump system exists. Detecting the leak includes alerting a user of the prosthetic device when the leak exceeds a threshold leak rate. Notification to one of either a patient or a prosthetist of a potential failure mode may be provided. Notification may include providing at least one of a visual or audible signal to a patient or a prosthetist to indicated the potential failure mode after a triggering event. The software allows the prosthetist to monitor multiple wearers in respective databases. Additionally, the software allows the wearer to select a method of low battery notification, which may include a vibration, audible beep, activated LED, or other method.

A power supply for the prosthesis may take the form of a rechargeable battery that does not require removal. As such, an internal battery may not be necessary as the pump system could draw power from a central power source located within the prosthesis that could power the pump system and other components. Additionally, the battery or other power source may not require direct contact to protect against environmental damage, such as moisture or non-liquid particulates. A multitude of charging options may be utilized including a hidden electrical outlet within the prosthesis or even possibly an underlying USB port that can be in connection with a computer as a charging source, as well as power generation strategies within the prosthesis. An induction coil may be utilized to generate power or recharge the battery. Also, power may be generated using a system that converts kinetic energy from the wearer.

An embodiment may include an easily operated on and off switch mounted inside the socket that activates at least the pump system when the prosthesis is donned. Another embodiment includes a switch on an exterior of the socket so that when a sleeve is placed over the socket the switch is activated. The exterior switch may also be activated directly by actions of the wearer. Additionally, the prosthesis may employ automatic on/off switching capabilities with a motion sensor that turns the pump system on for a period of time after sensing movement of the prosthetic limb, and off after period of time of no movement. The pump system may turn off automatically after a period of time in which no significant change in vacuum pressure is detected. Further, an additional backup on/off strategy may be employed to activate the pump system such as, but not limited to a key chain type remote, blue-tooth, cell-phone, etc. Motion of the limb may be monitored to initiate, sustain, or adjust the vacuum pressure or socket environment. For instance, as the wearer becomes more active, the vacuum pressure may be raised to account for the increase in activity, which may correlate to higher and/or more frequent loading. The wearer's activity level may be detected and monitored using a variety of sensors combined with other parameters, which may take the form of force, step counter, cadence variance related information, time clock, angle, angular change, angular velocity, accelerometer, or other known sensors found in the field of prosthetics and robotics.

In one embodiment, the pump system includes a piston or hydraulic mover, a motor, an actuator such as a linear actuator, a gear assembly cooperating with the actuator and motor, a vacuum chamber, one or more valves, wires, air tubes, a power supply, and one or more sensors to monitor pressure variations within the socket. A space between the pump system and the socket provides a region in which the vacuum pressure may be generated. The pump system may include a diaphragm-type pump, a rotary-style pump, an axial pump or another type of pump. In one embodiment, the pylon may be utilized as a cylinder instead of a separate glass airport, and a vacuum may be drawn against the pylon directly.

The pump system is preferably located within the pylon to save space within the prosthesis. All electronics and circuitry may be configured in such a manner that they fit within the pylon and be easily mounted to the prosthetic socket. Additionally, a method of affixing the components of the pump system to minimize or prevent undesired movement relative to movement of the prosthesis may include ties, clamps, fasteners, etc. Wires and tubes may as well exit the pylon as necessary to provide usability and access. The pylon may be sealable to make the prosthesis generally water resistant and thereby keep the components of the pump system sufficiently dry.

An axial pump may provide the desired vacuum pressure with only a few strokes of the piston. This low cycle operation may beneficially require less power and minimize any extraneous noise generated by the pump system.

The piston head of the piston may be flush with, space slightly from, or in light frictional contact with an inner wall of the pylon or accessory housing. The piston may move in the axial manner via any number of methods including but not limited to a helical worm gear system or linear actuator. A helical worm gear system operates in constant connection with the motor which may be of a rotary fashion. This may as well include a "reverse-double helix internal sliding glider hollow piston pump" or other known methods. Additionally, the helical worm gear may be attached to a piston which moves in relation to the movement of the helical worm gear. As the rotary motor turns it rotates the helical worm gear system in an upwards fashion and in turn forces the piston to move upwards. Once a full movement of the piston has been made a mechanism such as but not limiting to a clutch may be employed to allow for the downward motion of the piston to its starting position.

The actuator may be in contact with, and generate the force necessary to move the piston to generate the vacuum pressure. Alternatively, hydraulic actuators may be employed to initiate movement of the piston.

A vacuum chamber may be located in the socket above and proximate the piston. Depending on the force imposed by the piston, the vacuum pressure will fluctuate within the vacuum chamber based upon whether an upstroke or downstroke of the piston. In one embodiment, the piston may be oriented such that the upstroke forces air out of the socket. A seal may be disposed about the piston or piston head and cooperate with the pylon to provide an air-tight environment.

The pump system may include valves for restricting the flow of air into and out of the pump system. By way of example, a one-way valve may be placed within the vacuum chamber to control inward and outward airflow. Additionally or alternatively, two-way valves may be employed in a chamber below the piston to release or bleed air during piston operation. Optionally, the chamber below the piston may be open to the atmosphere.

The prosthesis may further include a non-digital computer regulator system for maintaining any chosen vacuum pressure range in the socket (see FIG. 6 below). The wearer may set the vacuum pressure through use of dials, knobs, or other sources to adjust desired vacuum range. The pump system may have one or more control circuits to set the lower and upper vacuum pressure range. For example, a single op-amp comparator circuitry turns the actuator ON when the pump system is initially powered.

Figure 6:
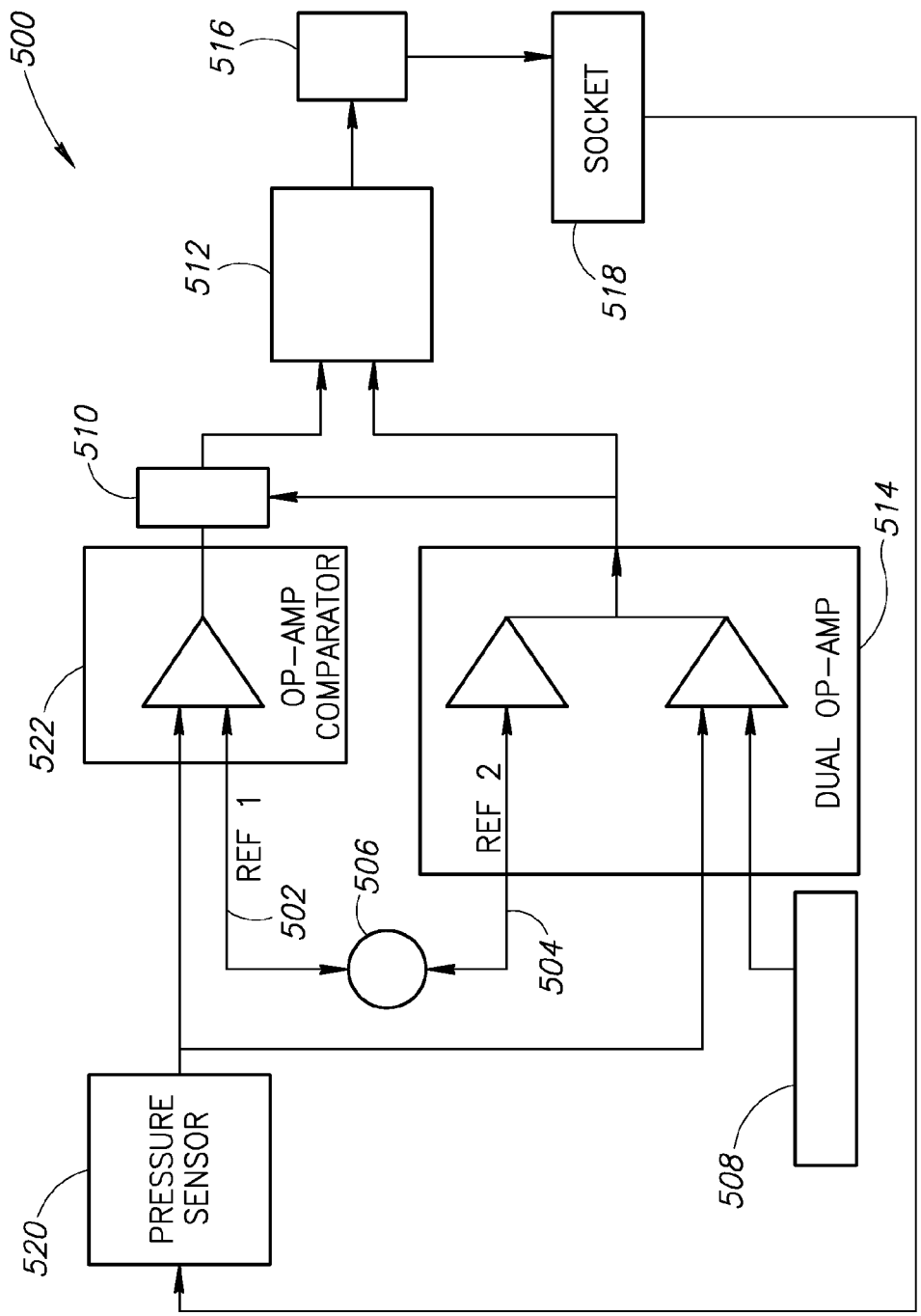
FIG. 6 is a general block plan of a preferred embodiment.
Figure 7:
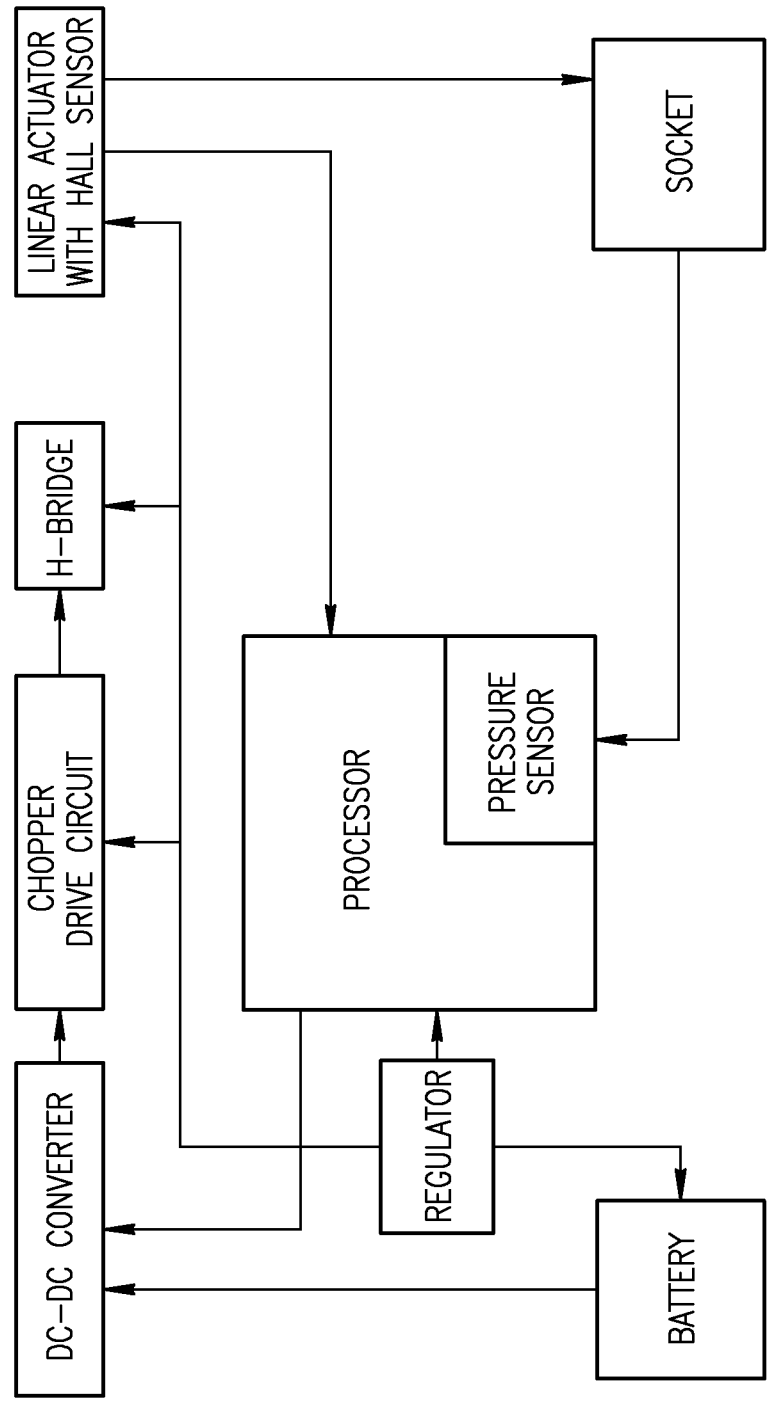
FIG. 7 is a general block plan of a preferred embodiment.

Referring briefly to FIG. 6, a logic diagram 500 shows a first reference voltage (Ref 1) 502 and a second reference voltage (Ref 2) 504, in which both may be at the same frequency. A control knob 506 sets a lower vacuum pressure for a pump system. Control knob 508 sets the upper limit of the vacuum pressure range. The prosthetist/wearer may set these knobs prior to starting the pump system. The knobs 506, 508 may also be adjusted while the pump system is on. There may be one or more switches and in the illustrated embodiment with first switch 510 being normally closed (NC) while second switch 512 is normally open (NO). Switch 510 may disconnect the startup circuitry as soon as the vacuum pressure reaches the lower range value. A voltage window detector circuit 514 having a dual op-amp system may then control an actuator 516 to keep the vacuum pressure in a desired range as detected in a socket 518 by a pressure sensor 520. The pressure sensor 520 may take the form of a differential vacuum sensor in communication with a chamber proximate to the socket, and where the sensor 520 includes one side open to atmospheric pressure. Input from the sensor 520 may be transmitted to or received by one or more circuits, such as an op-amp comparator circuit 522.

Controlling the pump system may be effectuated by employing wired or wireless communication devices such as, but not limited to, computer, handheld computer devices (e.g., PALM® or BLACKBERRY® systems), phone, watch, or other practitioner or wearer settable devices. These devices may be used to allow the practitioner or wearer to adjust setting parameters from time to time. In addition, the wearer may have a relatively limited number of options to adjust, whereas the practitioner or administrator of the prosthesis may have a broader range of use options.

FIG. 1 shows schematic side view of prosthesis 100 attachable to a residual limb 102, shown in dashed lines, and which may take the form of a transtibial residual limb. The prosthesis 100 includes a socket 104 configured to closely receive the residual limb 102 while providing a space 106 between a bottom surface 108 of the limb 102 and a bottom surface 110 of the socket 104. A pump system 112 is in fluid communication with the space 106 by way of a conduit 114, which may include a valve 116. The conduit 114 may take the form of flexible tubing while the valve 116 may take the form of a one-way valve, such as a check valve. The pump system 112 operates to exchange air with the space 106 as will be described in greater detail below.

A pylon 118 may be configured to house the pump system 112 or vice versa, meaning the pump system 112 may be configured to be received in the pylon 118. An optional cover 120, which may take the form of a cosmetic cover, may be arranged to substantially hide the pylon 118. In an alternate embodiment, the pump system 112 may be attached externally to the pylon 118, but still be sized such that it remains within a spatial envelop 122 defined between the cover 120 and the pylon 118.

The pylon 118 generally extends from the socket 104 to an artificial foot 124 for the illustrated example of the transtibial residual limb 102. It is appreciated that the prosthesis 100 may be configured to be attached to other types of residual limbs such as, but not limited to, transfemoral, transradial, and transhumeral limbs.

Whether during operation of the pump system 112 or at other times, it may be necessary to bleed or otherwise expel air from the pump system 112. In the illustrated embodiment, a bleed tube 126 provides fluid communication between the pump system 112 and the spatial envelop 122 if the cover 120 is included or otherwise ambient air if the cover 120 is not included. Vacuum pressure in space 106 is reduced by allowing air from space 122, or from the atmosphere, to enter space 106 through the bleed tube 126.

An acoustic muffling device 128 may be positioned in a flow path of the tube 126 to minimize audible airflow sounds.

Figure 2:
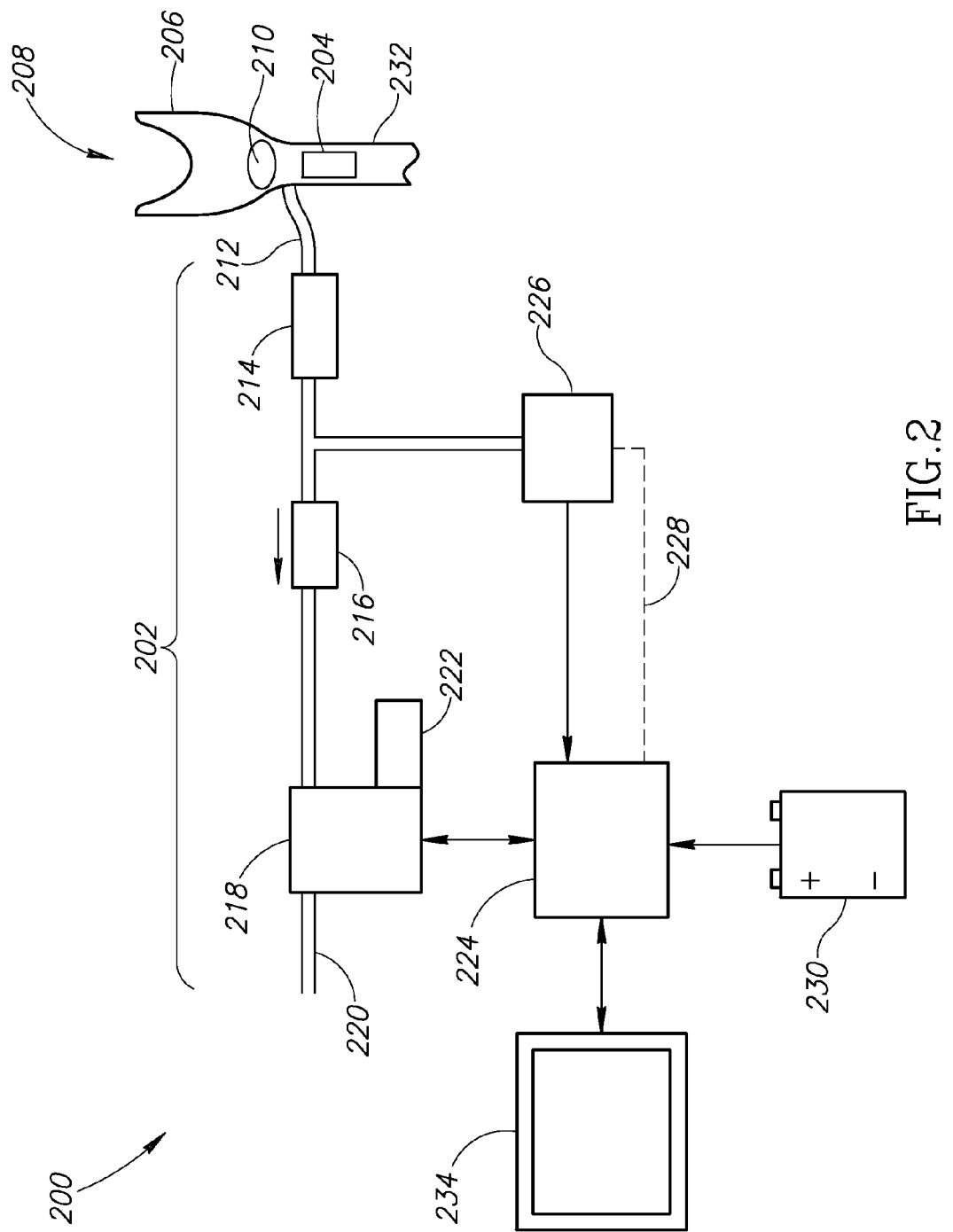
FIG. 2 is a general block plan of a preferred embodiment.

FIG. 2 schematically shows a pneumatic diagram 200 of a pump system circuit 202 for a pump system 204 in fluid communication with a socket 206 of a prosthesis 208. The pump system 204 may operate to draw a vacuum pressure from a space 210 within the socket 206 by drawing air the space 210 and through a conduit 212. A filter or membrane 214 may be located in a flow path of the conduit 212 to prevent or at least minimize extraneous particles from entering the pump system 204. The filter 214 may also be configured to reduce audible sounds associated with the air flow.

The drawn air may next pass through a one-way valve 216, which functions to keep the drawn air from reentering the socket 206. A vacuum pump 218 may provides the energy to draw the air from the space 210 of the socket 206. To maintain an adequate suspension of the prosthesis 208 the pump 218 does not have to continually operate. The valve 216 may be configured to regulate the vacuum pressure, which in turn may provide down time for the pump system 204. At least some of the drawn air may be expelled though an exhaust conduit or port 220. A backup or additional vacuum pump 222 may be included to boost the amount of drawn air, to increase a flow rate of the drawn air, or both depending on instructions received by the pump system circuit 202 by a control system 224.

A pressure sensor or transducer 226, which may measure or otherwise detect a differential pressure (i.e., the pressure difference between the drawn air and the ambient air) of the drawn air, may be in communication with the control system 224. The pump 218 may be controlled by the control system 224, which may receive and process signals 228 from the sensor 226. In one embodiment, the signals 228 may take the form of analog signals that are processed through an analog-to-digital module with a microprocessor (not shown). The analog signal 228 may include a voltage taken across the sensor 226. After processing of the signals 228 by the control system 224, instructions may be provided to the pump 218 to generate a stronger vacuum pressure, maintain a status quo, or reduce the vacuum pressure. The control system 224 may also receive and process information received from the socket 206 or other components of the prosthesis 208, for example the control system may receive information related to forces generated by the wearer in particular directions, moisture within the socket, for example from perspiration, and temperature data that may component specific, limb specific data or both. The circuit 202 may be powered by a battery 230, which may be located within a pylon 232 adjacent the pump system 204.

An external or remote computing system 234 may be utilized to communicate with the control system 224. The computing system 234 may be manipulated by the wearer, prosthetist, or even an artificially intelligent program to review data, change settings, change parameters, calibrate the prosthesis, transmit data, etc.

Figure 3:
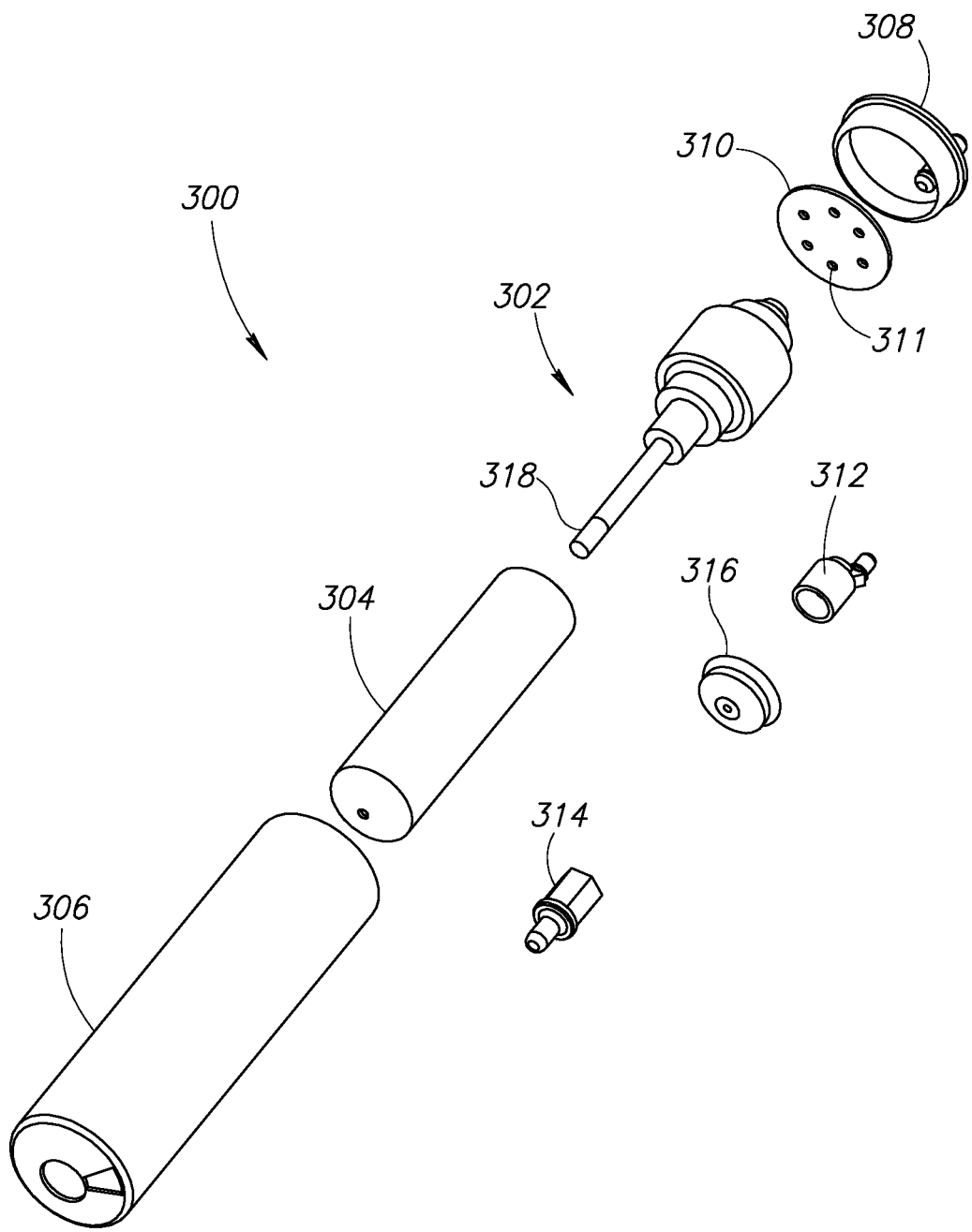
FIG. 3 is a general partially exploded cutaway view of a preferred embodiment of the invention.

FIG. 3 shows a perspective, partially exploded view of a prosthesis 300 without a socket for purposes of clarity and brevity. In the illustrated embodiment, a pump system 302 is received by a cylinder 304, which in turn is received by an outer casing 306. Advantageously, placing the pump system 302 into both the cylinder 304 and casing 306 may provide an acoustic barrier to substantially mute any pump related noise. The casing 306 may be made from a variety of materials such as, but not limited to, plastics, metals, ceramics, elastomers, and polymeric materials.

A detachable upper cap 308 may be mechanically coupled (threaded, bonded, press fit, etc.) to the casing 306 in an airtight and/or fluid-tight manner for the purpose of access to the pump system 302. The cap 308 may engage the casing 306 to provide a desired airtight seal. An outer perimeter surface of the cylinder 304 may be in contact with an inner surface of the casing 306 or there may be an air gap therebetween. Preferably, the air gap may be sized to provide the additional sound barrier as mentioned above. The cap 308 exhausts the air. Plate 310 having apertures 311 are for muffling the air as it is exhausted. The cap 308 may have a sound-dampening liner to further minimize pump related noise that could be audible to the wearer or others nearby. The liner may be made from a sound-dampening silicon material, a polymeric material, a fiber-reinforced resin-impregnated material, or other materials capable of providing some amount of sound-dampening. Sound-dampening may also be achieved by varying the mass and/or stiffness of the cylinder 304, the casing, or both.

Still referring to the illustrated embodiment of FIG. 3, a one-way valve 312 and barb 314 may be located within the casing 306 and preferably within the cylinder 304. The barb 314 permits fluid communication between the pump system 302 and the socket. Vacuum is achieved because a plunger 316 operated by a motor 318 draws in air from the socket and exhausts the air through the cap 308.

Figure 4:
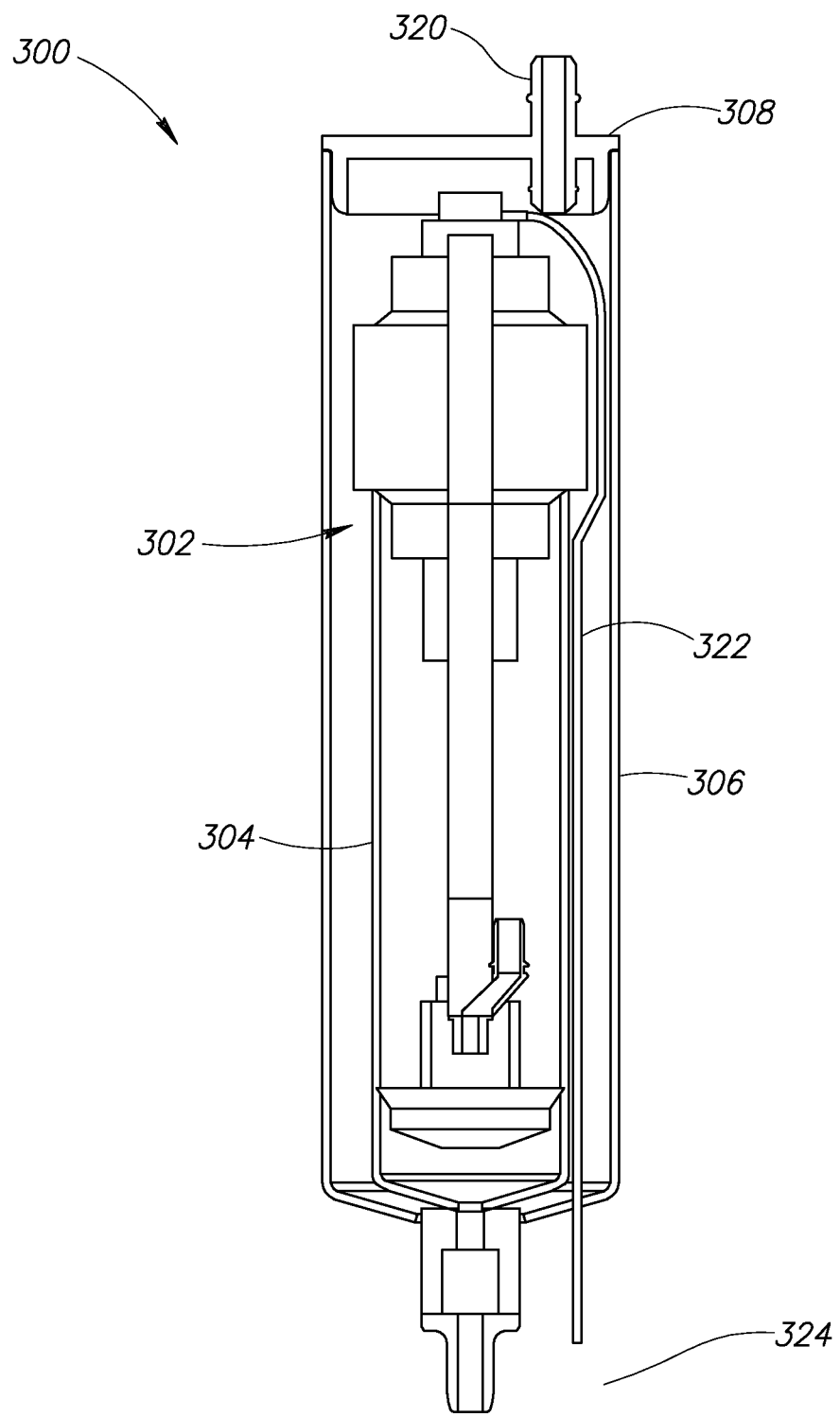
FIG. 4 is a general view of a preferred embodiment.

FIG. 4 shows the prosthesis 300 described above, still without the socket, but with the other components in an assembled configuration. In the illustrated embodiment, the pump system 302 is partially received in the cylinder 304 and both are housed within the casing 306. The detachable end cap 308 is sealably engaged with the casing 306. A conduit 320 extends from the end cap 308 to be in fluid communication with the socket (not shown). One or more tubes 322 may be positioned within the casing 306 to provide an airflow pathway from the conduit 320 to the ambient air 324.

The prosthesis may include sound-dampening components and construction such at a sound decibel level of audible noise detectable outside of the pylon or casing may be less than fifty decibels (50 dB).

Figure 5:
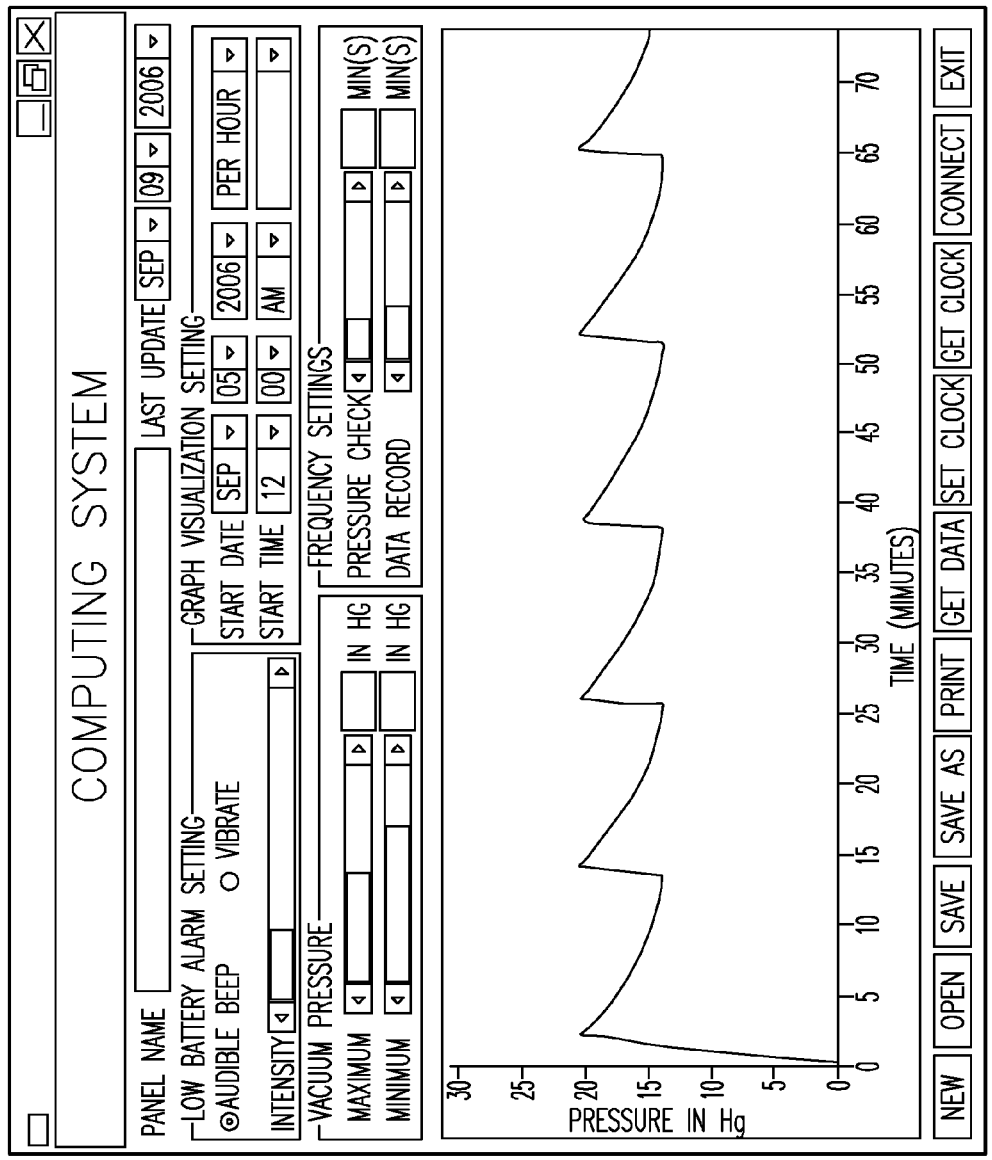
FIG. 5 is a general view of a graphic wearer interface that may control the settings of the prosthesis.

The prosthesis may include circuitry that interacts with a Graphical User Interface (GUI) 234 such as illustrated in FIG. 5. The GUI interacts with the control system 224 (FIG. 2).

The prosthesis may include circuitry equipped with the ability to monitor and record various functions of prosthesis usability. The prosthesis may include a sealing mechanism such as a dual layer liner, or other sealing device which is incorporated to encourage a maximal vacuum environment. The prosthesis may include a power source, which in one embodiment may be located externally to a pylon and provide a primary source of power for multiple applications and/or components.

The prosthesis may include a pressure controlling mechanism to control a relative level of vacuum pressure in response to applied forces and conserve power. The pressure controlling mechanism may also alter the socket environment according to environmental needs such as moisture and temperature. A non-digital computer regulator may be included to adjust the vacuum pressure and perform other functions.

The prosthesis may include an ON/OFF to automatically shut the pump system or other components off when not in use. The switch may be triggered by a reduction in vacuum pressure for a pre-determined amount. In one embodiment, at least some of the components of the prosthesis are arranged to provide at least some dampening of audible sounds generated by at least the pump system, for example.

The prosthesis may include a microprocessor or digital computer for synchronizing various electronics, circuits, software programs or modules, processors, databases while further interacting with a graphical user interface (GUI). This interaction may be accomplished with a variety of interfaces such as, but not limited to, a wireless interface using single or multi-channel wireless communication system.

The invention may include a vacuum source, wherein a vacuum is generated from said vacuum source that may be located internal within a pylon.

The pump system of the prosthesis may include a linear actuator or a linear piston pump. The pump system may further include an actuator connected to a piston and used to generate vacuum. The actuator may be in direct contact with a piston, which in turn may be sealed to be substantially air-tight. The pump system may be actuated by an electro-active polymer or artificial muscle. The pump system may include a solenoid operable to generate the vacuum pressure. Further, the pump system may have a controllable, bidirectional shaft to generate the vacuum pressure.

Figure 8A:
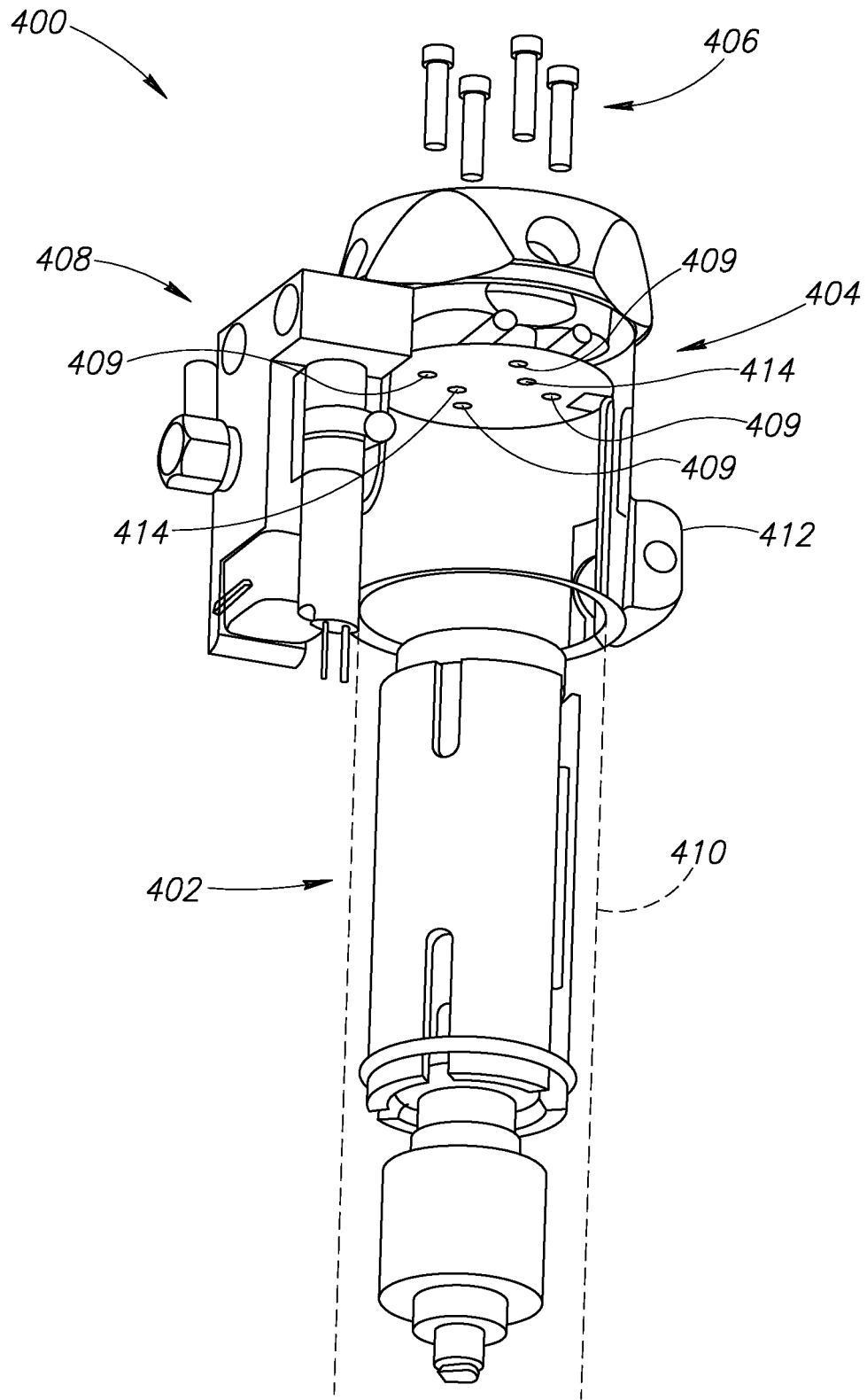
FIG. 8A is a perspective view of a pump system according to an embodiment of the present invention.

FIG. 8A shows a vacuum pump system 400 having a vacuum engine 402 mounted to a tube clamp adaptor 404 with mounting screws 406. A manifold 408 is attached to the adaptor 404 through four openings 409 and is in fluid communication with the vacuum engine 402 through ports 414, and the openings 409 and ports 414 may be located in close proximity of each other as indicated in the illustrated embodiment. The manifold 408 houses a pressure transducer to measure pressure and also houses a solenoid valve that may be opened to bleed air back into a socket (not shown). The adaptor 404 attaches a pylon 410 to the socket. In FIG. 8A, the pylon 410 is shown schematically with dashed lines so the vacuum engine 402 may be seen with more clarity. The vacuum engine 402 is secured to the adapter 404 using the screws 406. Openings 414 in the adaptor 404 provide mounting locations for the screws 406 and provide air exchange ports between the vacuum engine 402 and the manifold 408. An external barb (not shown) communicates with the manifold 408 and is the fluid communication with the socket.

Figure 8B:
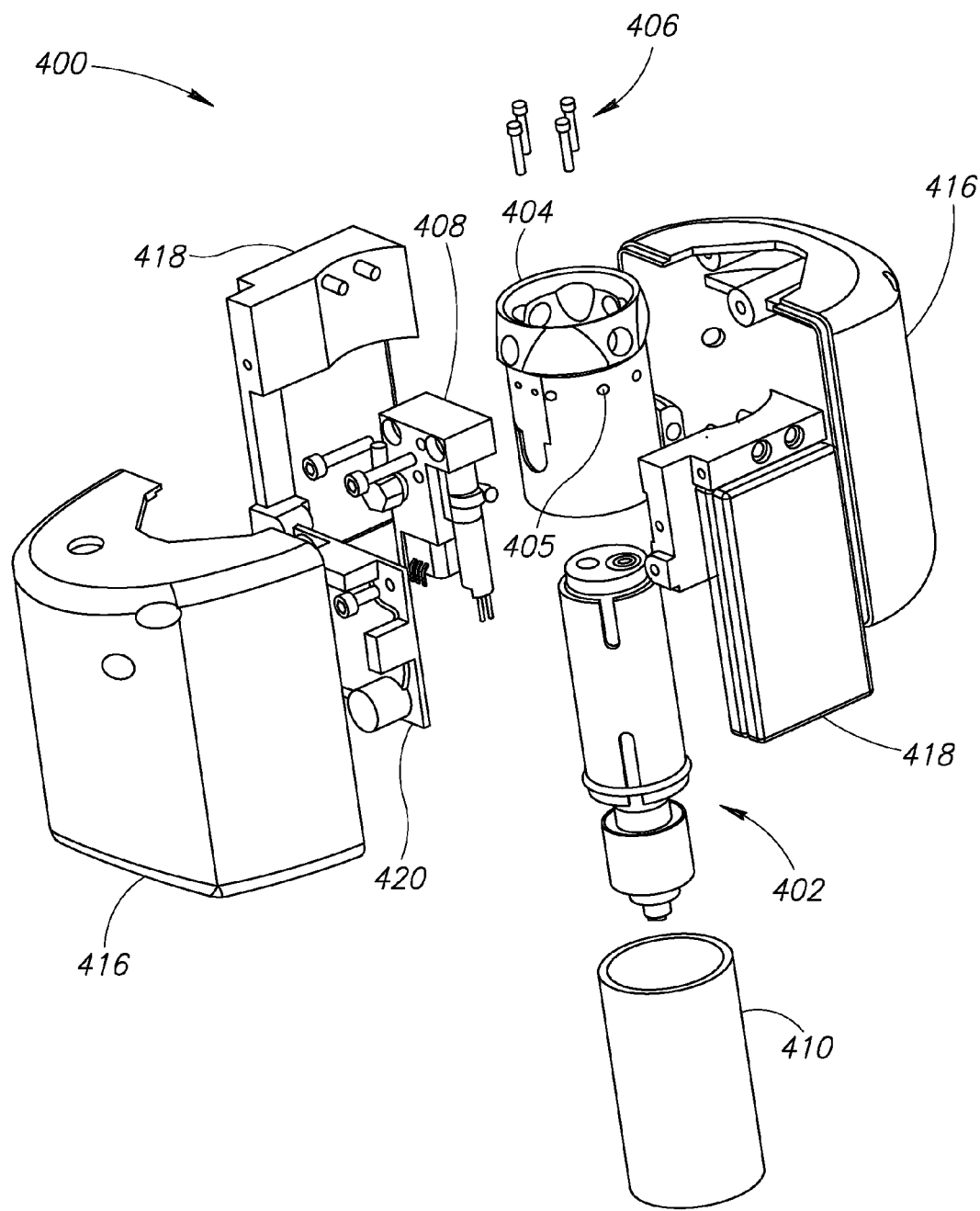
FIG. 8B is a partially exploded, perspective view of the pump system of FIG. 8A in relationship to a pylon for housing the pump system according to an embodiment of the present invention.

FIG. 8B shows an exploded view of the vacuum pump system 400 from FIG. 8A. The pylon 410 is pushed over the vacuum engine 402 and into the adaptor 404, which is then tightened around the pylon 410. Therefore, the vacuum engine 402 is located within the cavity defined by the hollow pylon 410, but not coupled to it directly.

The system 400 further includes covers 416 to protect the other components of the system 400 mentioned above. In addition, battery mounts 418 may be positioned within the covers 416 and mounted directly to the adaptor 404. Control circuitry 420, which may take the form of a circuit board, is mounted to the battery mounts 418. The control circuitry 420 may function to monitor pressure, activate the motor in the vacuum engine 402 and perform other tasks depending on its corresponding control algorithms or programs.

Figure 9:
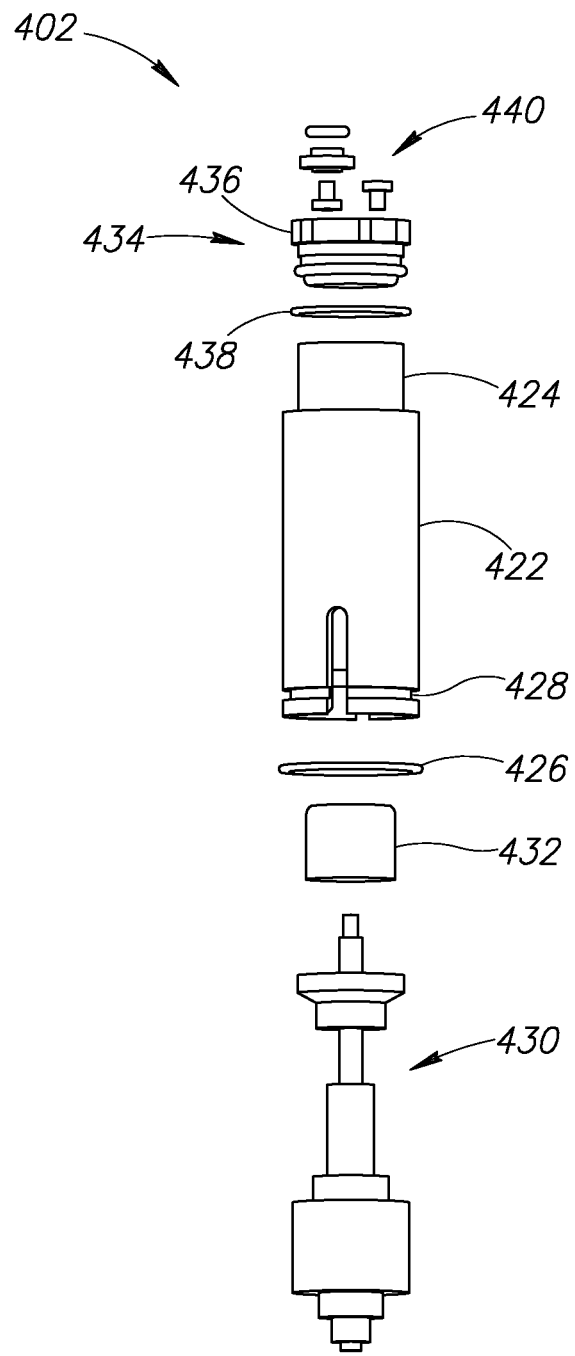
FIG. 9 is an exploded, side elevational view of a vacuum engine for a pump system according to an embodiment of the present invention.

FIG. 9 shows the vacuum engine 402, which includes a cylinder cover 422 that fits over a glass cylinder 424 that defines the vacuum chamber therein. A valve seal 426, which may take the form of an o-ring seal, is positioned in a seal groove 428 formed in the cover 422. The cylinder cover 422 may serve as the motor connection to the valve seal 426. A motor 430 operates a low friction graphite piston 432 to change or maintain pressure in the cylinder 424. The low friction graphite piston 432 preferably includes a tight tolerance fit within the glass cylinder 424 creating the necessary vacuum seal. A valve assembly 434 is located on the cylinder 424 and a valve head 436 may operate to suspend the motor 430 through an upper o-ring snap fit 438 and cylinder cover 422. The upper o-ring may also act as a vibration isolator with respect to the operation of the motor 430. The valve assembly 434 includes one-way valves 440 for exchanging air with the socket.

In one embodiment, the pump system includes a maximum outside diameter of about 0.90 inches, which allows the pump system to fit within a variety of prosthetic pylons. Locating the pump system within the pylon helps minimize audible sounds generated by the pump system. In addition, the pump system may be directly coupled to the adaptor, which in turn may be coupled to the pylon using compliant mounts, vibration isolators, elastomeric materials, etc. to minimize selected modes of vibration and minimize the transfer of vibrational loads to other prosthetic components. Preferably, the pump system cannot be felt or heard by the wearer when in operation. The pylon acts as a sound dampener in addition to providing structural protection for the pump system.

The motor 430 may include a rechargeable battery as a primary power supply and preferably the motor battery does not need to be removed from the prosthesis to be recharged. Alternatively, the battery may be coupled to or otherwise supported by the battery mounts 418, which are enclosed by the covers 416. The covers 416 may take the form of an elastomeric cover to protect the battery from water or other environmental damage. A low battery indicator may be incorporated into the protective housing. The indicator may take the form of a light emitting diode (LED) to alert the wearer of the low battery condition.

A push-button ON/OFF switch may be mounted on the cover 416 and may be activated by the wearer. In one embodiment, the switch is recessed in the cover 416 to prevent bumping of the switch on objects, which could turn the pump system ON or OFF unexpectedly.

Figure 10A:
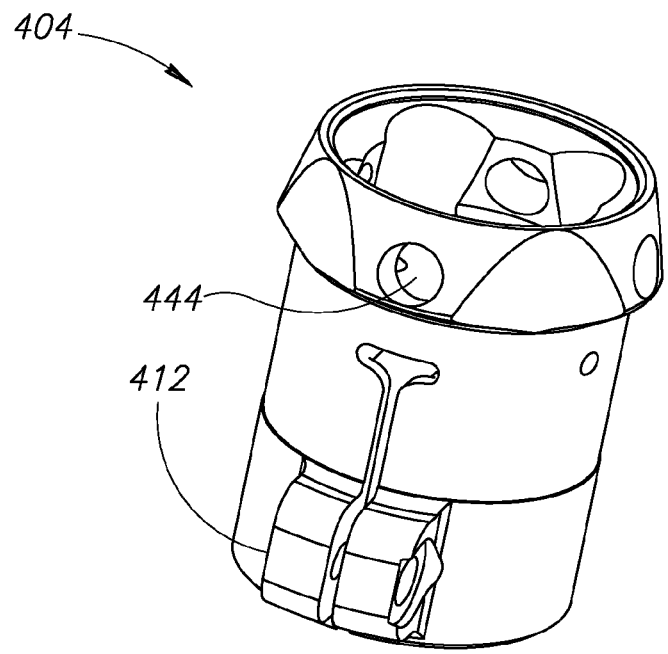
FIG. 10A is a perspective view of an adaptor according to an embodiment of the present invention.
Figure 10B:
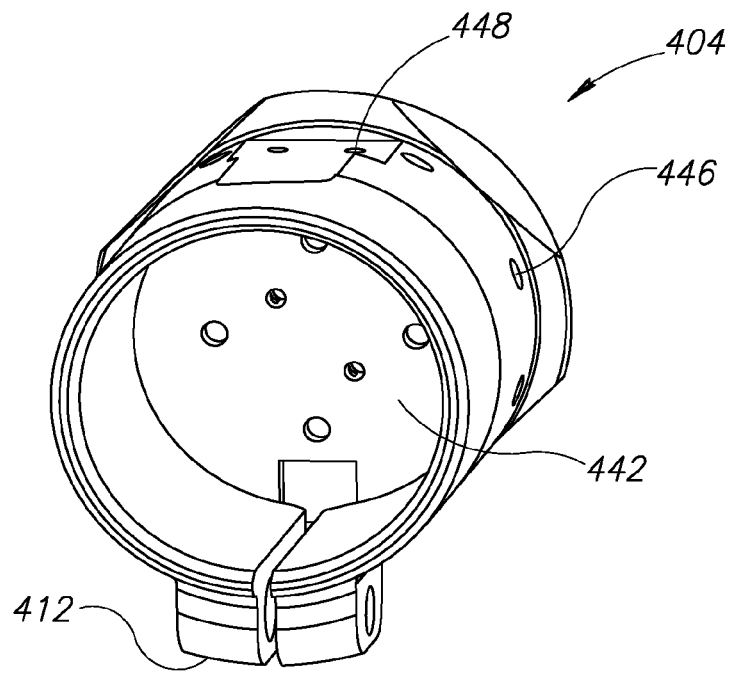
FIG. 10B is a perspective, end view of the adaptor of FIG. 9A.

FIGS. 10A and 10B shows the adaptor 404 having an interface plate 442 with the openings 414. The adaptor 404 operates as a structural mounting platform for the vacuum engine 402, pylon 410, covers 416, battery mounts 418, the circuit board 420, and optionally other components (e.g., sensors, filters, power sources, etc.). Set screw openings 444 are configured to secure the adaptor 404 to a standard pyramid that attaches to a bottom of the socket. Side mounting holes 446 receive the battery mounts 418 while other holes 448 permit fluid communication between the vacuum engine 402 and the manifold 408.

Figure 11:
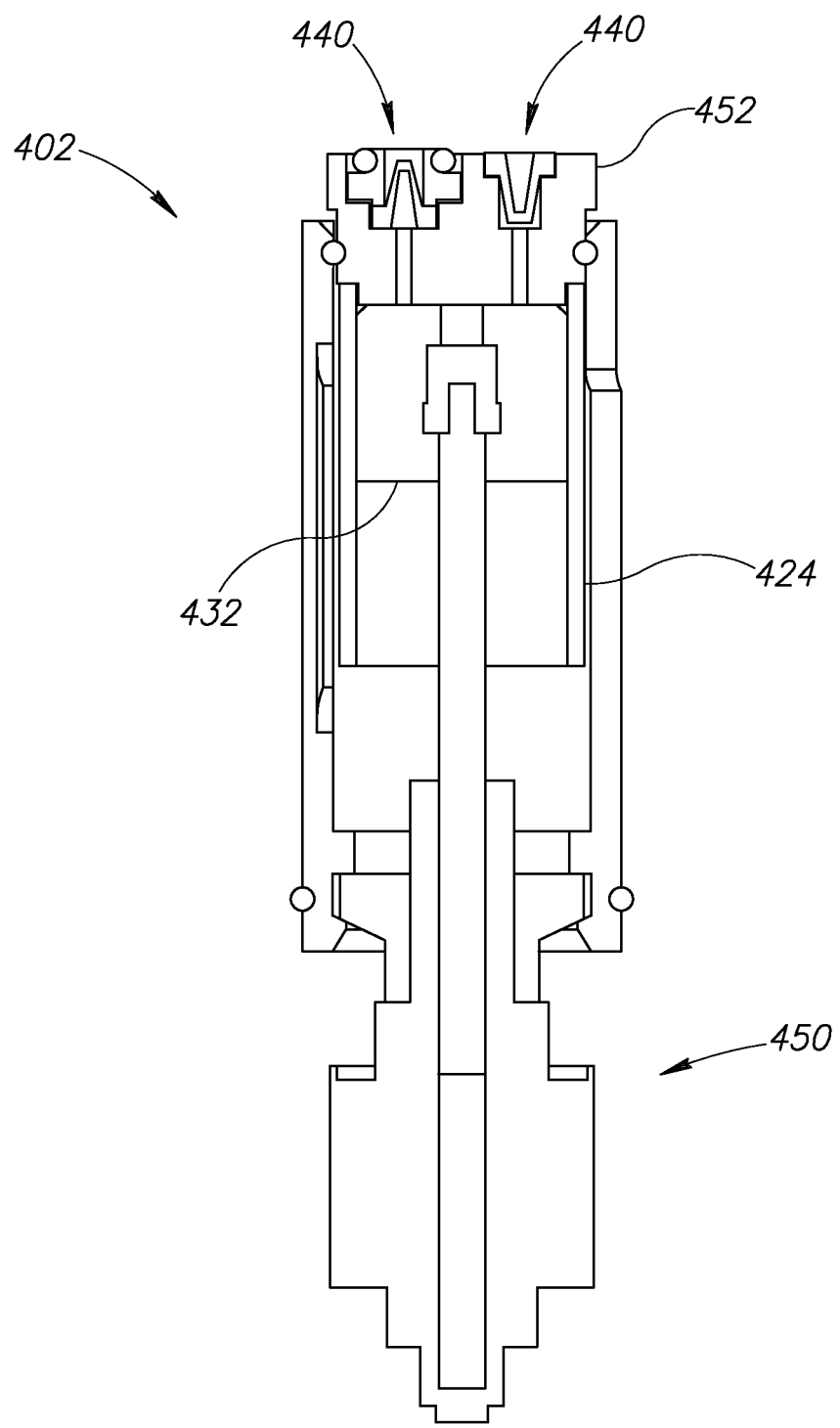
FIG. 11 is a cross-sectional view of a vacuum engine according to an embodiment of the present invention.

FIG. 11 shows the vacuum engine 402, which may take the form of a large volume displacement pump having a linear actuator 450 driving the piston 432 within the cylinder 424. The large volume displacement pump may have a pumping capacity of greater than 0.25 cubic centimeters per minute (>0.25 cc/min.). In one embodiment, the linear actuator 450 drives the piston 432, which is made from a low friction material (e.g., graphite) or includes a low friction coating, inside the cylinder 424, which takes the form of a glass cylinder, and more preferable a PYREX® cylinder. The linear actuator 450 may be configured to reduce sound and vibration of the motor without compromising performance and the low friction interaction between the piston 432 and cylinder 424 permits the motor to be smaller and still smoothly step, microstep, maintain a desired velocity, and to accelerate or decelerate in a desired manner. The vacuum engine 402 may include a filter to minimize, if not prevent, any undesired exchange of liquids or particulates between the socket (not shown) and vacuum chamber. In addition, the vacuum engine 402 includes one-way valves 440, which may permit the ingress or egress of air between the socket and vacuum chamber defined by the cylinder 424. The valves 440 may be formed in an end closure 452 of the vacuum engine 402.

Figure 12:
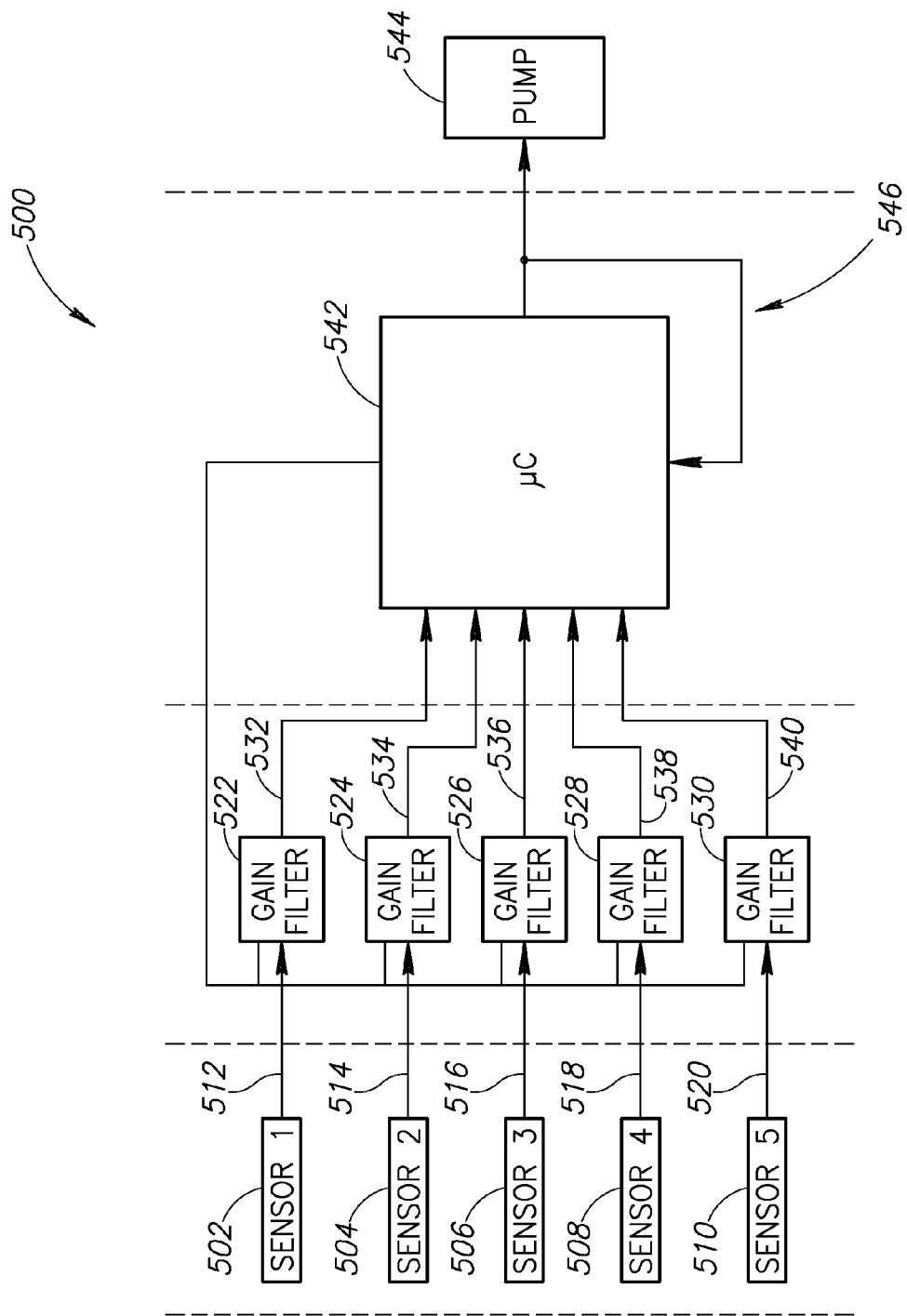
FIG. 12 is a diagram of a control system for a prosthetic according to an embodiment of the present invention.

FIG. 12 shows a control system 500 that adopts a multi-variant, multi-parameter model as an overall control scheme. In one embodiment, the control system 500 uses multiple concurrent sensory inputs indicated as reference numerals 502-510 and these sensory inputs may take the form of pressure sensors, accelerometers, strain gauges, goniometer/angular measurement sensors, gyroscopes, EMG, etc. to evaluate gait and movement, determine the activity and level of activity, and set the pressure limits within the socket that are determined to be appropriate for a specific activity. The output signals 512-520, respectively, may be operated on by gain filters 522-530, as necessary. In turn, the filtered signals 532-

540 are fed into a pump control processor or microprocessor 542 that controls a pump 544 via a feedback loop 546. It is appreciated that the number of sensory inputs and corresponding signals may be greater or fewer than the number shown in the illustrated embodiment.

An algorithm utilized by the processor 542 may be configured to process patterns detected by the filtered signals 532-540 and then analyze these signals using a fuzzy logic algorithm that not only qualifies pressure data and number of steps, but also predicts or presumes specific activities and an exertion level for one or more of the specific activities. The fuzzy logic algorithm may also determine inactive states where the patient might be sitting or other sedentary activities, which in turn may prompt the microprocessor 542 to command the pump 544 to vent air into the socket to make the fit of the prosthetic more comfortable for the wearer. Advantageously, the control system 500 may optimize overall control and provide for faster response times with regard to pressure levels in the socket as a function of a rate of change in the wearer's activity. In one embodiment, the fuzzy logic algorithm may command the pump and/or other components of the prosthetic to enter a sleep mode during times of inactivity in an effort to conserve electrical power, increase working time and reduce the size of the power source.

In one example of the control system 500 in which the wearer is primarily sedentary, such as in a seated position, the control system 500 receives data consistent with the wearer's state through the input sensors 502-510, which would result in a command from the microcontroller 542 to activate the pump 544 to reduce the pressure to a pre-configured or desired comfort level given the sedentary condition. In another, slightly more complex example, the wearer may be walking at various gaits, each gait speed requiring a different level of pressure to maintain good fit. The dynamic response time and minimal lag time of the control system 500 permits the microprocessor 542 to continually provide adjustment commands to the pump such that the wearer may barely sense a change in the fit of the prosthetic at the various gait speeds. In a more complex example, the fuzzy logic algorithm processes synthesized orthogonal data streams for what may be considered as higher exertion level physical activities such as, but not limited to, biking, rowing, swimming, hiking, orienteering, etc. For such higher exertion activities, the fluctuations in a particular dataset (e.g., socket pressure) may not correspond directly with a desired pressure level that indicates a good fit (FIG. 13) to the wearer. Biking, for instance might mimic aggressive walking, but typically prosthetics users only "push" on the pedals and thus the highest level of pressure would not be required. Similarly, fast dancing might have pressures and accelerations that would exceed the normal speed of walking or even running accompanied by lateral and vertical movements not typically encountered by the prosthesis, but might require the control system 500 to maintain a high pressure level in the socket. By synthesizing multiple data streams, a complete picture of the wearer's activity may be captured and the appropriate pressure levels achieved. A known activity may be identified from a pre-programmed database of known activities. A known activity may be selected by identifying the known activity from a non-static database.

Figure 13:
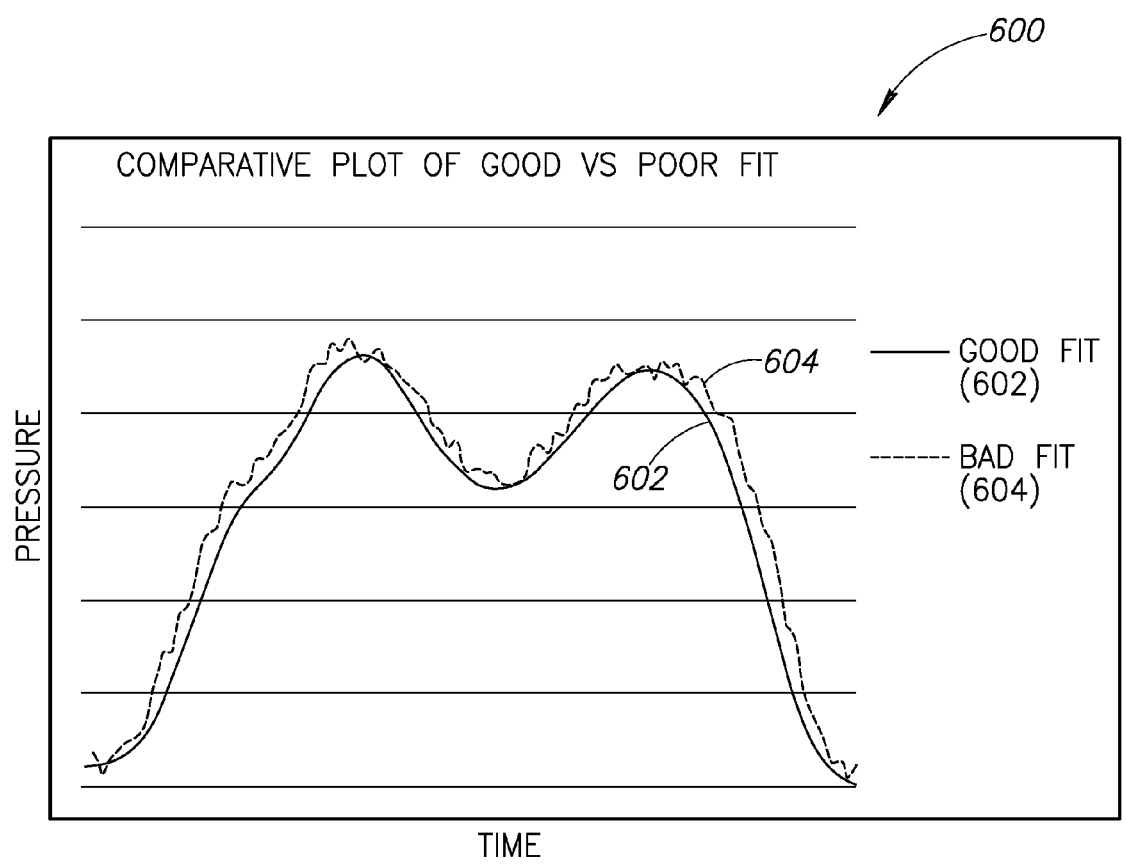
FIG. 13 is a chart comparing pressure data for a good prosthetic fit versus a bad prosthetic fit as controllable by a control system according to an embodiment of the present invention.

FIG. 13 shows a chart 600 having prosthetic fitting curves of pressure changes in the socket using a pattern recognition technique of the fuzzy logic algorithm in the control system 500. Smooth curve 602 shows a "good fit" throughout a variety of gait cycles and stances while choppy curve 604 shows a "bad fit" having discontinuities or rapid slope changes. For example, the bad fit indicates pressure changes going from a stance to a swing or vice-versa as well as additional noise due to movement and adjustment of the residual limb within the socket. This goodness of fit measurement can be used as a clinical diagnostic tool to guide the necessity for socket adjustment or a new socket.

The algorithm may also use an analytical model based on the positive displacement pump dynamics as part of overall control scheme. By comparing a theoretical model to measured data, the control system 500 may predict not only the quality of fit at donning, but provide safety margins for battery life by closely estimating the actual power expenditure in real time throughout the wear cycle based on one or more activities.

While the preferred embodiments of the invention have been illustrated and described, as noted above, many changes can be made without departing from the spirit and scope of the invention. Accordingly, the scope of the invention is not limited by the disclosure of the preferred embodiments. Instead, the invention should be determined entirely by reference to the claims that follow.

The embodiments of the invention in which an exclusive property or privilege is claimed are defined as follows:

1. A method of controlling a prosthetic vacuum suspension device, the method comprising:
   sensing, by a pressure sensor, a pressure level in a prosthetic socket and controlling the pressure with a pump located within a pylon of the prosthetic device;
   sensing, by at least one of a temperature sensor and a humidity sensor, at least one of temperature and humidity;
   determining, by a control device coupled to the pressure sensor and the at least one of the temperature sensor and the humidity sensor, a first present activity pattern based on both of the sensing of the pressure level by the pressure sensor and the sensing of the at least one of temperature and humidity by the at least one of the temperature sensor and the humidity sensor;
   selecting, by the control device, a first known activity pattern from a plurality of activity patterns based on the first present activity pattern such that the first known activity pattern is selected based on both the sensing of the pressure level and the at least one of temperature and humidity, the first present activity pattern having first pressure levels;
   adjusting, by the control device, pressure limits for the pressure level in the prosthetic socket to first pressure limits for the first known activity pattern;
   determining, by the control device coupled to the pressure sensor and the at least one of the temperature sensor and the humidity sensor, a second present activity pattern based on both of the sensing of the pressure level by the pressure sensor and the sensing of the at least one of temperature and humidity by the at least one of the temperature sensor and the humidity sensor;
   selecting, by the control device, a second known activity pattern different from the first known activity pattern from the plurality of activity patterns based on the second present activity pattern such that the second known activity pattern is selected based on both the sensing of the pressure level and the at least one of temperature and humidity, the first present activity pattern having second pressure levels mimicking the first pressure levels; and
   adjusting, by the control device, pressure limits for the pressure level in the prosthetic socket to second pressure limits for the second known activity pattern, the second pressure limits being different from the first pressure limits.

2. The method of claim 1, further comprising sensing at least one non-pressure parameter from a sensor selected from a group of sensors consisting of accelerometers, strain gauges, goniometers, gyroscopes, transducers, and thermocouples and selecting the known activity pattern based on all of the sensing of the pressure level, the sensing of the at least one of temperature and humidity, and an output of the at least one non-pressure parameter.

3. The method of claim 1, wherein determining the present activity includes analyzing signals from the sensors with at least one controller.

4. The method of claim 1, wherein determining the present activity pattern includes conditioning signals from the pressure sensor and the at least one of the temperature sensor and the humidity sensor.

5. The method of claim 1, further comprising sensing a force in the prosthetic device.

6. The method of claim 1, further comprising sensing a displacement by a portion of the prosthetic device.

7. The method of claim 1, wherein selecting the known activity includes identifying the known activity from a pre-programmed database of known activities.

8. The method of claim 1, wherein selecting the known activity includes identifying the known activity from a database.

9. The method of claim 1, wherein selecting the known activity includes downloading the known activity from a computer system that is remotely located from the prosthetic device.

10. The method of claim 1, further comprising detecting a leak of fluid from the prosthetic socket during the present activity.

11. The method of claim 10, wherein detecting the leak includes alerting a user of the prosthetic device when the leak exceeds a threshold leak rate.

12. The method of claim 1, determining the present activity includes putting the system in a low power quiescent mode when the present activity detects a low demand for suspension force.

13. The method of claim 1, further comprising providing notification to one of either a patient or a prosthetist of a potential failure mode.

14. The method of claim 13, wherein notification includes providing at least one of a visual or audible signal to a patient or a prosthetist to indicated the potential failure mode after a triggering event.

15. The method of claim 1, further comprising sensing at least one of force and load on the prosthesis.

16. A method of controlling a prosthetic vacuum suspension device, the method comprising:
sensing, by a pressure sensor, a pressure level in a prosthetic socket and controlling the pressure with a pump located within a pylon of the prosthetic device;
sensing, by a temperature sensor, temperature;
sensing, by a humidity sensor, humidity;
determining, by a control device coupled to the pressure sensor, the temperature sensor, and the humidity sensor, a first present activity pattern based on all of the sensing of the pressure level, temperature, and humidity;
selecting, by the control device, a first known activity pattern from a plurality of activity patterns based on the determined present activity pattern such that the first known activity pattern is selected based on all of the sensing of the pressure level, temperature, and humidity, the selecting the first known activity pattern including inputting all of an output of the temperature sensor, an output of the humidity sensor, and an output of the pressure sensor into a selection algorithm;
performing a first adjusting, by the control device, pressure limits for the pressure level in the prosthetic socket based on pressure limits for the first known activity pattern;
determining, by the control device a second present activity pattern based on all of the sensing of the pressure level, temperature, and humidity;
selecting, by the control device, a second known activity pattern from the plurality of activity patterns based on the determined present activity pattern such that the known activity pattern is selected based on all of sensing the pressure level, temperature, and humidity, the selecting the second known activity pattern including inputting all of the output of the temperature sensor, the output of the humidity sensor, and the output of the pressure sensor into the selection algorithm; and
performing a second adjusting, by the control device, of the pressure limits for the pressure level in the prosthetic socket based on pressure limits for the second known activity pattern;
wherein the pressure limits for the second known activity pattern are different from the pressure limits for the first activity pattern; and
wherein the first and second present activity patterns are not distinguishable from one another based exclusively on the sensing of the pressure level by the pressure sensor.

* * * * *